United States Patent [19]

Hurson

[11] Patent Number: 5,711,669
[45] Date of Patent: Jan. 27, 1998

[54] HIGH LOAD FACTOR TITANIUM DENTAL IMPLANT SCREW

[76] Inventor: Steven M. Hurson, 5610 Van Gogh Way, Yorba Linda, Calif. 92887

[21] Appl. No.: 747,226

[22] Filed: Nov. 12, 1996

[51] Int. Cl.[6] ........................................ A61C 8/00
[52] U.S. Cl. ........................................ 433/174
[58] Field of Search ........................ 433/172, 173, 433/174, 175, 176, 177

[56] References Cited

U.S. PATENT DOCUMENTS

| | | | |
|---|---|---|---|
| 5,180,303 | 1/1993 | Hornburg et al. | 433/174 X |
| 5,181,850 | 1/1993 | Neumeyer | 433/205 |
| 5,478,237 | 12/1995 | Ishizawa | 433/174 |
| 5,482,463 | 1/1996 | Wilson, Jr. et al. | 433/174 X |
| 5,605,457 | 2/1997 | Bailey et al. | 433/174 |

*Primary Examiner*—Nicholas D. Lucchesi

[57] ABSTRACT

A dental prosthesis system comprising a titanium dental implant, a dental implant and a titanium screw coated with a biocompatible material that is malleable or subject to cold flow and is sufficiently softer than titanium that such material will, upon application of torque to the screw, deform and be largely displaced without any deformation of the titanium screw is disclosed.

7 Claims, 1 Drawing Sheet

HIGH LOAD FACTOR TITANIUM DENTAL IMPLANT SCREW

FIELD OF THE INVENTION

This invention relates to dental prostheses and, more particularly, to screws used to secure a prosthesis to an implant wherein both the implant and the screw are made of titanium

BACKGROUND OF THE INVENTION

Titanium, and its biocompatible alloys, referred to herein simply as titanium, is the material of choice for surgical implants generally and for dental implants specifically. Titanium offers a combination of nearly ideal characteristics—high strength, light weight, biocompatibility and essentially total resistance to corrosion in contact with tissues and bones. Modern machining methods and powder metallurgical techniques make it possible to manufacture fine surgical components of very high precision.

However, titanium joints, e.g. screw threaded joints, tend to seize and the high friction of the material reduces the percent of the applied force that is actually applied to tightening the joint, a substantial portion of the force being wasted overcoming the coefficient of friction. This is particulary true in titanium-titanium joints.

In circumstances involving large components, large screws and bolts, etc., the frictional disadvantage can often be overcome by applying very large tightening forces. Even this solution is limited, however, by the strength of the components. The problem is particularly critical where small screws, bolts, etc., are involved because the breaking point of the components may not be much greater than the forces resulting from friction.

Tooling for tightening the screws may break, or the hex head or recess may give away, if the forces required to accomplish satisfactory preloading are excessive.

These problems have been recognized in various industrial applications and several solutions have been suggested.

Tightening of screws, including titanium screws, with controlled pre-stressing force often poses problems, especially in light-gauge construction. The coefficient of friction is decisive for calculating the pre-stressing force. Screw surface treatments such as Cd-plating, anodic oxidation, nitriding and Al coating improve the conditions of friction. (Turlach, G., Schraubenherstellers, Bander Bleche Rohre 30, (3), 50–54 March 1989 (Abstract))

Tightening efficiency is largely a function of the antifriction properties of the joints. A titanium alloy joint strength is increased about on combined use of Cu coating and $MoS_2$ based lubricant. (Zmievskii, V I; Zamilatskii, E P, Vestn. Mashinostr. (10), 29–31 October 1986 (Abstract))

The coefficient of friction can be reduced to prevent seizing in the threaded connections of titanium alloys. Antifriction coatings of soft Cadmium have been recommended. (Sorokin, V. M; Shtulov, D. I; Tsvetkov, V I, Khim. Neft. Mashinostr. (6), 27–28 1979(Abstract))

Hard coatings on titanium and its alloys are known to reduce wear in a variety of environments, e.g.: Titanium nitride coatings on steel machine parts, (Su, Y L; Lin, J S, Wear 170, (1), 45–53 15 Nov. 1993 (Abstract)), in machinery for processing plastics that contain abrasive particles, (Matthes, B; Broszeit, E; Kloos, K H, 19th International Conference on Metallurgical Coatings and Thin Films, San Diego, Calif., USA, 6–10 Apr. 1992, Surface and Coatings Technology 57, (2–3), 97–104 28 May 1993 (Abstract)), in metal cutting tools and dies, (Schadlich, S, Wire 42, (1), 166–169 Feburary 1992, (Abstract)) and Schostek, H., U.S. Pat. No. 4,949,836.

Japanese Patent No. 4066213 (Abstract) describes a seizure preventive coating formed on titanium or titanium alloy by heating the alloy to form an oxide layer, making a screw tool by cold forging the titanium or titanium alloy rod, to make semi-complete screw tool. The oxide film is then removed by polishing and acid pickling followed by form rolling to complete a screw tool. The screw tool is said to have good corrosion and heat-resistance, and good luster. The method is used in the manufacture of bolts and nuts.

The importance of forming hard surfaces on prosthetic joints to increase wear and produce a low-friction joint is, of course, well-recognized, see, e.g., Wagner H, et al., U.S. Pat. No. 5,133,769, which discloses surgical appliance in the form of a cap for fitting over the end of the femur in a hip joint prosthesis is in the form of a hemispherical shell with the outer surface being made from a wear resistant cobalt alloy and the inner surface being made from titanium. In this environment, the joint is well-lubricated by biological fluids in the joint area.

While there are many variations in the mechanisms and methods by which a dental prosthesis is installed in a patient's jaw, the following are suitable examples of prior art methods and structures. The fixture is the component which is surgically placed into the jawbone; this is often accomplished by a periodontist or oral surgeon. After a healing period of a few months, during which a process of bone growth around the fixture called osseointegration occurs, the implant is exposed. A general dentist or prosthodontist then performs the restoration, which involves placement of an abutment of a specific size and shape over the fixture and securing the same by means of a bolt threaded into a cavity in the fixture. The implant distal surface contains a flat, polished outer ledge and a central hex which is then engaged by a tool during placement. Also indicated by the prior art is a submucosal healing cap and a transmucosal healing cap which prevent the fixture from becoming infiltrated with tissue from the gingiva and/or bone. In addition to keeping tissue out of the fixture the healing cap establishes a sulcus or opening above the fixture to allow placement of the second component, the abutment.

The abutment is secured into the threaded cavity of the fixture by a titanium bolt, called the abutment retaining screw. The prosthesis is the third component of the system; this element is fabricated of cast gold alloy and porcelain. However, since machined parts have greater accuracy than cast parts, the prosthesis is commonly cast to a machined component which is fastened to a threaded cavity in the abutment by a retaining screw. Gold, and gold alloy screws, are well-known. This gold screw, being smaller and of weaker alloy than the titanium abutment retaining screw, should normally be the first to fracture if excessive force is encountered.

One modification of the above system is to attach the prosthesis directly to the fixture without any intervening abutment. This method uses only the large titanium screw.

A further variation is to cement a restoration to implants in the same manner as is done in conventional fixed bridges on natural teeth. In this case, a tapered abutment without threads, often referred to as a cementable abutment, is fastened to the fixture with a large titanium abutment retaining screw. Thus, this method also has only one screw in the system.

To summarize, implant dentistry relies upon screws to fasten together component stacks. These stacks consist of the fixture, abutment, and prosthesis (commonly fabricated around a machined gold cylinder). A second possibility consists of just the fixture and prosthesis eliminating the abutment for reasons of esthetics, angulation, etc. A third possibility consists of an abutment to which the prosthesis is cemented.

Screws have been used in dental prostheses for more than two decades and the problems of using screws have been studied in depth, see, e.g. Burquette, R. L., et al., The Journal of Prosthetic Surgery, June 1994, 71:592–599.

The purpose of tightening any screwed joint is self-evident; if a screw is not tight it cannot achieve the function of clamping together component parts. However, the appropriate level of tightness required in a particular situation is much less obvious, although a specific torque is recommended for each screw in the implant system. The long-held belief has been that to avoid loosening of the screw, the torque applied when tightening the screw should be as high as possible.

Initially external forces applied to the screwed joint, for instance, during chewing, lead to the effective erosion of the preload in the screwed joint. The screw can be thought of as a spring, stretched by the preload, for which the stretch is maintained by the friction forces in the threads. Any transverse or axial external force that causes a small amount of slippage between the threads, no matter how small, releases some of the stretch and some of the preload is lost. At this stage the greater the joint preload (up to a maximum equal to the ultimate strength), the greater will be the resistance to loosening, because the friction formed between the threads will be greater and a large external force is required to cause slippage. In the second stage of loosening, the preload is below a critical value so that external forces and vibrations cause the mating threads to turn or "back off". Once this stage has been reached, the screwed joint ceases to perform the function for which it was intended and has failed.

The other major consideration in selecting an appropriate level of tightness is the fatigue life of the screw. If the screw is tightened until it is "snug tight," meaning all mating parts of the joint are in contact, then the screw or bolt will experience all of the external load applied to the clamped parts to separate them. However, as the tightening torque is increased above the snug tight level, the preload increases and the screw or bolt will gradually receive increased protection against the external load. This protection is increasingly beneficial to the fatigue performance of the screw until the total load experienced by the screw as a result of the preload and the external load is approximately equal to the yield of the screw. When this load level is exceeded, the fatigue performance of the screw decreases drastically.

Screws used as fasteners can loosen when subjected to cyclic or vibratory loads. Such loads certainly occur in the mouth. This loosening can be viewed more accurately as slippage of the entire joint, which consists of the two components involved and their fastening screw.

Consequences of screw loosening in the general case are:
Repeated loosening of the restoration. If the frequency is months or weeks the loosening becomes unacceptable to both the patient and the dentist.
Screw or abutment retaining screw bending.
Screw or abutment retaining screw fracture.

While these problems with the fastener do not occur in the majority of implant cases, their frequency is sufficient that the causes are being actively investigated.

In some instances, the system is overloaded, for instance by placing too few implants for the number of teeth being replaced. In these cases, screw fracture or bending is the most preferable outcome, because it gives the clinician warning that the system is being overloaded. Screw bending or fracture is less of a problem than abutment retaining screw bending or fracture, since the screw is most easily retrievable. Abutment retaining screw fracture can be dealt with by removing the fragment of the abutment retaining screw contained within the threaded cavity in the fixture. This procedure is usually difficult and can even irreversibly damage the fixture. Fixture fracture or failure of osseointegration is the least desirable outcome of overload, as these imply loss of the fixture. If the screw breaks, there is still time to reconsider the placement of fixtures and the design of the prosthesis and make corrections, perhaps by adding more fixtures.

Screws are also known to loosen in many cases that are well designed, have sufficient fixtures and appear to fit very accurately. These instances of screw loosening are due to vibration, defined as low but highly repetitive forces on the joint. Vibration has a tendency to loosen bolts and screws. It has been postulated that very small movements of the implant prosthesis, termed micromovements, occur in response to vibration and increase the chance of screw loosening. This is at least part of the motivation to cement restorations; note, however, that there is still a screw in the cementable abutment.

When a screw is tightened, a tensile force, termed the preload, is built up in the screw, mainly between the head and the first few threads. This preload is what holds the components of an implant component stack together. The screw is placed in tension, and the components fastened by the screw are placed in compression. Preload also prevents loosening of the screw. The preload should be as high as possible (for a given tensile strength of the screw material) and should fluctuate as little as possible to prevent loosening.

Occlusal forces from chewing, speaking, bruxing, etc. (which can be viewed as vibrations) load the prosthesis and place forces on abutment retaining screws and gold screws which may result in loosening of the screws. If the screw loosens, the preload is decreased or lost, the screw joint opens up, and the screw will then loosen further, bend or break. Once permanent deformation takes place, either through wear-and-tear effects or through gross bending, there is nothing to prevent the screw from loosening.

Additional effects act on screws to reduce preload. When any implant screw is tightened for the first time, contact between its threads and the screw channel walls only occurs on microscopic areas of roughness. Plastic flow of these initial contact points occurs and reduces preload. This phenomenon is called embedment relaxation or settling effects. Thus, the torque used to place a retaining screw initially is greater than that required to remove it.

One proposed solution to screw loosening is using high torque or torque within a certain range in the placement of the various retaining screws. However, what constitutes the proper torque has not been determined by controlled scientific investigation. Also, the torque required to loosen an implant screw is less than that used to tighten it, due to settling effects and wear-and-tear effects on the screw threads. High initial torque may not prevent screw loosening months or years after placement, due to wear-and-tear effects and the cyclic loading that occurs in the mouth. Even if an ideal initial torque could be determined, it has been shown that dentists vary widely in their ability to place a screw within a specified torque range. Mechanical torque drivers are necessary to achieve consistency, but this application only relates to initial torque values, not those achieved after settling effects and cyclic loading. Very high torque may create torsional stress on the screw beyond safe limits, leading to permanent deformation and fracture. Thus, placing screws with high torque is not an ideal solution to the problem of retaining screw loosening in well-designed implant cases.

Spring washers of the helical, split-lock type and/or Belleville washers work on many levels to help prevent screw loosening.

A spring washer placed under the screw head maintains a constant tension in the screw, decreasing the chance of loosening under cyclic or vibratory loads. The spring washer acts as a damping mechanism for micromovement, preventing transmission of that movement into the screw.

Washers act to distribute loads and provide a surface for uniform torque control. By increasing the preload and the clamping forces, spring washers may make the screw joint more resistant to opening up and subsequently bending or fracturing.

Some of the kinetic energy of screw tightening is converted into potential energy in the spring of the washer; thus, spring washers store energy. This energy adds to the preload. Another way in which washers add to preload is more subtle. For hard metal screws and screw channels, up to 90% of the applied torque is used to overcome the friction forces caused by the screw threads and under the screw head. Washers represent dry lubrication. Reducing the coefficient of friction of the screw in its channel and/or under the screw head acts, according to the principles of operation of fasteners, to increase the preload of the screw for a given applied torque. Consequently, the possibility of loosening is decreased significantly. The increased preload also reduces the working stresses in the components held together by the screw, decreasing the possibility of fatigue failure due to cyclic stress.

The effect of reducing the coefficient of friction and/or the collar radius of the screw head is to increase the preload for a given torque. This avoids the problems of extremely high torque placement of screws, which places high torsional stress on the screw and weakens it. In other words, for a given torque, one can have higher preload with a washer.

One final way of thinking about lockwashers is to examine what fraction of a full turn of a retaining screw it takes to dump all of the preload out of the system. In current implant practice, a very small turn of the screw, perhaps as little as 1/32 of a turn, would be sufficient to eliminate most of the preload. With a lockwasher of appropriate torsional stiffness, a significant fraction of preload could be maintained even if the screw was backed off 1/4 or 1/2 of a turn. This arrangement would allow more leeway, in terms of time, to intervene before loosening and damage took place.

A split-lock type lockwasher in various modifications placed between the healing cap and the fixture has been described. An opening in the gingiva (gum) is created surgically and preserved by use of the healing cap body. The cap is intended to pass through the gingiva to the outer surface of the surrounding gingiva. The underside of the cap is shaped in various modifications to provide a cavity or flat surface which accepts a lockwasher. The lockwasher is of the split-lock, helical type. The cap is installed on the implant by threading a separate screw into the threaded base of the implant with the lockwasher in between until the proximal surface of the cap is in contact with the washer, which is in contact with the distal surface of the implant.

U.S. Pat. No. 5,482,463, Wilson, Richard S., et. al., describes a screw joint for dental implant component stacks which has greater resistance to loosening, and therefore greater resistance to bending and/or breaking. This effect is accomplished by the use of spring washers and modifications to the screw and screw channel in implant components. The screw is driven into a threaded channel in the abutment retaining screw, and the head of the screw fits in a channel within the gold cylinder and bears on a flat surface of the gold cylinder. This widens both the radius of the screw head and the channel in the gold cylinder. A helical split-lock washer or Belleville washer is placed between the screw head and the flat bearing surface of the gold cylinder. This has the effect of increasing the preload and of increasing resistance to slippage of the entire joint, for the reasons discussed above.

While the use of springs, as described by Wilson, et. al., provides a partial solution to the long-standing problem of loosening of screws in dental implants, the fundamental problem of low preloading remains largely unsolved.

It has long been recognized that it would be desirable to provide a dental prosthetic system which took advantage of the strength of titanium without the loss of a high preload advantage resulting from the high friction of a titanium to titanium screw joint.

Efforts to provide such a system using hard-surface screws, e.g. nitride or carbide surfaced titanium screws, have not only failed to permit the formation of a high preload titanium screw joint but, generally, have been less satisfactory than the use of uncoated and untreated titanium screws.

Conventional lubricants are, of course, entirely unacceptable for use in prosthetic implants.

The object of this invention is to provide a prosthesis system in which the prosthesis is secured to a titanium implant with a specially coated or treated titanium screw which secure the prosthesis under a condition of high screw preloading.

SUMMARY OF THE INVENTION

It has been discovered that titanium screws coated or treated with selected biocompatible materials can mount a prosthesis in a titanium implant under a high preload without the application of unacceptable torque, thereby providing an implant system that is less susceptible to loosening under stress, vibration or other conditions of use.

In general, screws coated or surface treated to comprise a layer of biocompatible material substantially softer than titanium which is malleable and/or subject to substantial cold-flow are suitable for use in this invention.

DESCRIPTION OF THE PREFERRED EMBODIMENTS

Figure 1:
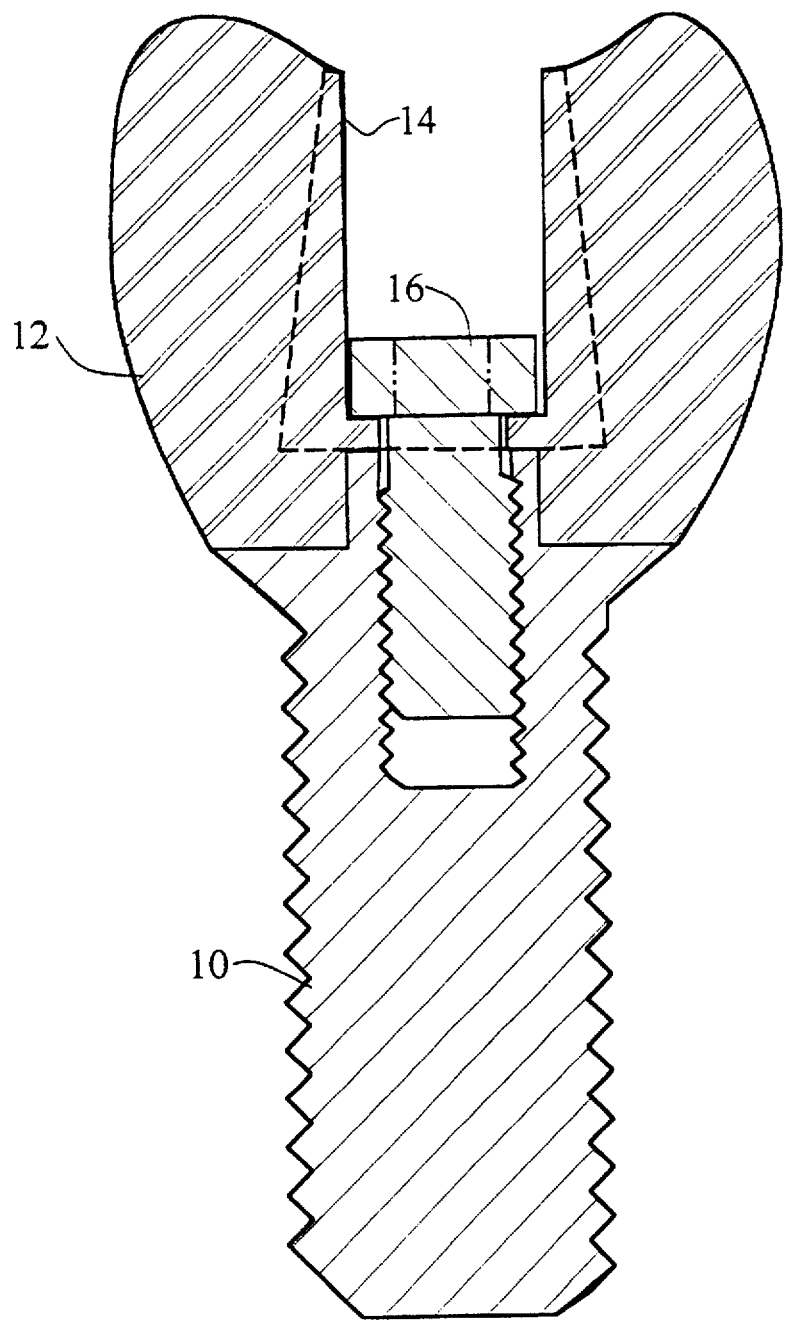
FIG. 1 depicts in a generalized way, in cross-section, a titanium dental implant to which a prosthesis is secured by titanium screw coated or treated in accordance with this invention. The configuration of the implant and prosthesis are generalized and are intended to represent any type of implant and/or prosthesis rather than any particular implant and/or prosthesis.
Figure 2:
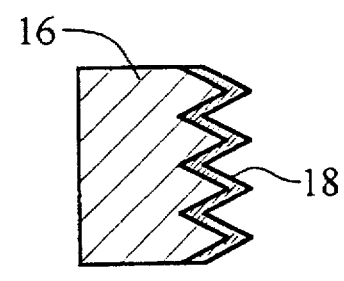
FIG. 2 depicts, greatly enlarged, a cross-section of a portion of the screw threads of the screw of this invention.

The drawing and the description refer to an exemplary embodiment of the invention and the drawing depicts in a general way an implant and a prosthesis, all of which are intended to permit a clear description of the invention and not to limit the invention to any particular implant or prosthesis. Indeed, it is contemplated that the best implant for the particular patient and the best implant coating or treating technology will be used and that the prosthesis will be configured in the most advantageous manner to meet the patient's dental prosthetic needs.

With the foregoing in mind, reference is made to FIG. 1 which depicts a titanium implant 10 of any desired configuration to which is secured a prosthesis 12. In this example, the prosthesis is mounted on an abutment 14; however, the prosthesis may be mounted using any device or structure which utilizes a screw attachment. The prosthesis and abutment are secured to the implant by a titanium screw 16 which, as shown in FIG. 18, has a surface covered with a soft biocompatible material 18. Exemplary of such materials are gold, silver and polytetrafluoroethylene bonded so firmly to the surface of the titanium as to be essentially non-removable under mechanical forces. Electrostatic coating, sputtering and other methods for producing such coatings are well-known, in a general sense, and are suitable for use in making the screws of this invention.

The biocompatible material 18 is very much softer than titanium and is malleable or tends to cold-flow. Such biocompatible material will deform and, upon application of sufficient force, be largely displaced by plastic deformation without any deformation of the titanium occurring. Another requirement is that the coating or surface treating material be so inextricably bound to the titanium screw threads that it cannot be removed by mechanical forces encountered in a screw thread joint. It is also important that the coating or surface treating material be sufficiently thick that upon plastic deformation of the material the torque forces are substantially evenly distributed along a substantial portion of the screw thread, rather than concentrated on the higher portions of the inherent roughness of the threads.

Two metal coatings are particularly advantageous as coatings for the titanium screw. Gold and silver are both sufficiently biologically inert to be used as coatings and neither alloys with titanium to a significant degree, i.e., the surface is essentially pure gold or silver, or an alloy of gold or silver, if such alloy is used as the coating.

One polymer is particularly advantageous. Polytetrafluoroethylene is a self-lubricating polymer and is sufficiently biocompatible for use in this application. Biocompatibility in the context of this invention means that the material is not significantly reactive with biological fluids or tissue, i.e. it is not corroded or otherwise degraded. Since the coating material is not in direct contact with tissue, it need not be as compatible as, for example, the material of which the implant is made.

Other polymers that may be used include polyethylene and polypropylene, nylon, polyacetals such as delrin, polyethylene terphthalates such as Mylar® and polycarbonates.

Alloys of gold and silver with each other or with other noble metals or with minor amounts of non-noble metals may be used provided the alloy is sufficiently soft,as described above.

The foregoing are merely exemplary and other materials are known or easily identified as being equivalent.

Metal and metal alloy coatings can be applied in any of the many methods known for depositing thin coatings of metal on metal. Vapor deposition, vacuum sputtering, chemical reaction deposition, electrolysis and ion implantation are exemplary of such methods. Many fine texts and treatises describe these processes and the technical literature is replete with examples of such methods and countless specific applications of these methods.

Organic polymers may, depending on the polymer, be deposited from a solvent system, sprayed, vapor deposited, catalytically formed on the surface, or simply applied from a melt of the polymer. Again, there are many general and specific teachings of coating materials with polymers in the literature which are well within the skill of the art.

The invention does not reside in the method of coating, but rather in the system that comprises three components: a titanium implant, a coated titanium screw ans a prodthesis or, equivalent insofar as this invention is concerned, a mount for a prosthesis, secured to the titanium implant by the coated titanium screw.

Industrial Application

This invention is useful in the dental prosthesis and implant industries.

What is claimed is:

1. A dental prosthesis system comprising a titanium dental implant having formed therein a threaded orifice, a titanium screw in the threaded orifice, and a coating on the titanium screw consisting essentially of a malleable biocompatible material that is sufficiently softer than titanium that upon application of torque to the screw such material will deform and be displaced without deformation of the titanium screw.

2. The invention of claim 1 wherein the coating material comprises gold.

3. The invention of claim 1 wherein the coating material comprises silver.

4. The invention of claim 1 wherein the coating is so thick that upon deformation thereof the torque forces are substantially evenly distributed along a substantial portion of the screw thread.

5. A dental prosthesis system comprising a titanium dental implant having formed therein a threaded orifice, a titanium screw in the threaded orifice, and a coating on the titanium screw consisting essentially of a polymeric biocompatible material that is sufficiently softer than titanium that upon application of torque to the screw such material will cold flow and be displaced without deformation of the titanium screw.

6. The invention of claim 5 wherein the coating material is polytetrafluoroethylene bonded so firmly to the surface of the titanium as to be non-removable when the screw is torqued.

7. The invention of claim 6 wherein the coating is so thick that upon cold flow thereof the torque forces are substantially evenly distributed along a substantial portion of the screw thread.

* * * * *